US006127145A

United States Patent [19]

Sutliff et al.

[11] Patent Number: 6,127,145
[45] Date of Patent: Oct. 3, 2000

[54] PRODUCTION OF $\alpha_1$-ANTITRYPSIN IN PLANTS

[75] Inventors: Thomas D. Sutliff, Rocklin; Raymond L. Rodriguez, Davis, both of Calif.

[73] Assignee: Applied Phytologics, Inc., Sacramento, Calif.

[21] Appl. No.: 09/023,339

[22] Filed: Feb. 13, 1998

Related U.S. Application Data

[60] Provisional application No. 60/037,991, Feb. 13, 1997.

[51] Int. Cl.$^7$ .............................. C12P 21/06; C12P 21/04; C07H 21/02; A01H 5/00
[52] U.S. Cl. ........................ 435/69.1; 435/69.7; 435/69.8; 435/70.1; 536/23.1; 536/23.6; 536/24.1; 800/320; 800/320.2
[58] Field of Search ................................ 536/23.1, 23.6, 536/24.1; 800/205, DIG. 52, 320, 320.2; 435/69.1, 69.7, 69.8, 70.1

[56] References Cited

U.S. PATENT DOCUMENTS

| | | | |
|---|---|---|---|
| 5,460,952 | 10/1995 | Yu et al. | 435/69.1 |
| 5,543,576 | 8/1996 | Van Ooijen et al. | 800/317.3 |
| 5,650,307 | 7/1997 | Sijmons et al. | 435/69.6 |
| 5,677,474 | 10/1997 | Rogers | 800/288 |
| 5,689,052 | 11/1997 | Brown et al. | 205/349 |
| 5,714,474 | 2/1998 | Van Ooijen et al. | 514/44 |
| 5,716,802 | 2/1998 | Sijmons et al. | 435/69.1 |

FOREIGN PATENT DOCUMENTS

| | | |
|---|---|---|
| 0 348 348 | 12/1989 | European Pat. Off. . |
| WO 90 01551 | 2/1990 | WIPO . |
| WO 91 02066 | 2/1991 | WIPO . |
| WO 92 01042 | 1/1992 | WIPO . |
| WO 95/14099 | 5/1995 | WIPO . |

OTHER PUBLICATIONS

Potrykus. Ann. Review of Plant Physiol. 1991. vol. 42: 205–225.

Wan and Lemaux. Plant Physiol. 1994. vol. 104: 37–48.

Hayashimoto et al. Plant Physiol. 1990. vol. 93: 857–863.

Bollen et al. DNA. 1983. vol. 2(4): 255–264.

Huang et al. Plant Molecular Biology. 1993. vol. 23: 737–747.

O'Neill et al. Molecular and General Genetics. 1990. vol. 221: 235–244.

Perlino et al., "The Human $\alpha^1$-Antitrypsin Gene is Transcribed from Two Different Promoters in Macrophages and Hepatocytes," *EMBO J.* 6:2767–2771 (1987).

Chan, M–T., et al., "Novel gene expression system for plant cells based on induction of $\alpha$–amylase promoter by carbohydrate starvation," J. of Biological Chemistry 269(26):17635–17641 (1994).

Jensen, L.G., et al., "Transgenic Barley expressing a protein–engineered, thermostable (1,3–1,4)–$\beta$–flucanase during germination," Proc. Natl. Acad. Sci. USA 93(8): 3487–3491 (1996).

Terashima, M., et al., "Production of functional human $\alpha$–1–antitrypsin by rice cell culture; expression and protein secretion in callus culture (conference abstract)," Abstr. Pap. Am. Chem. Soc. Abstract #018, ACS National Meeting, Las Vegas, NV, Sep. 7–11 (1997).

Thomas, B. R., et al., "Gene Regulation and Protein Secretion from the Plant Cell Cultures: The Rice $\alpha$–Amylase System," Advances in Plant Biotechnology pp. 37–55 (1994).

*Primary Examiner*—Lynette R. F. Smith
*Assistant Examiner*—Ousama M-Faiz Zaghmout
*Attorney, Agent, or Firm*—Joanne R. Petithory; Peter J. Dehlinger

[57] ABSTRACT

A method for producing $\alpha_1$-antitrypsin (AAT) in plant cells is disclosed. Monocot plant cells transformed with an AAT coding sequence are cultivated under conditions efficient for protein expression and secretion. Also disclosed are a codon-optimized AAT coding sequence that is efficiently translated in plant cell culture and a novel AAT protein having the glycosylation pattern characteristic of plant cells and suitable for therapeutic use in humans.

9 Claims, 11 Drawing Sheets

```
              10            20            30            40            50            60
     c   g        c   c   c                  c   c   c ag        c   c        c        g
GAG GAT CCC CAG GGA GAT GCT GCC CAG AAG ACA GAT ACA TCC CAC CAT GAT CAG GAT CAC CCA
Glu Asp Pro Gln Gly Asp Ala Ala Gln Lys Thr Asp Thr Ser His His Asp Gln Asp His Pro>

70            80            90           100           110           120
     g                      g   t tt    c     a                    g                c   g
ACC TTC AAC AAG ATC ACC CCC AAC CIG GCT GAG TTC GCC TTC AGC CTA TAC CGC CAG CTG GCA
Thr Phe Asn Lys Ile Thr Pro Asn Leu Ala Glu Phe Ala Phe Ser Leu Tyr Arg Gln Leu Ala>

130           140           150           160           170           180
                      tc        c                 ag    g              c   c        c   c
CAC CAG TCC AAC AGC ACC AAT ATC TTC TTC TCC CCA GTG AGC ATC GCT ACA GCC TTT GCA ATG
His Gln Ser Asn Ser Thr Asn Ile Phe Phe Ser Pro Val Ser Ile Ala Thr Ala Phe Ala Met>

190           200           210           220           230           240           250
     g             t         g        c         c   g         c   a   c         c       g
CTC TCC CTG GGG ACC AAG GCT GAC ACT CAC GAT GAA ATC CTG GAG GGC CTG AAT TTC AAC CTC
Leu Ser Leu Gly Thr Lys Ala Asp Thr His Asp Glu Ile Leu Glu Gly Leu Asn Phe Asn Leu>

260           270           280           290           300           310
              c             g             c   g                 g   g   a g   g
ACG GAG ATT CCG GAG GCT CAG ATC CAT GAA GGC TTC CAG GAA CTC CTC CGT ACC CTC AAC CAG
Thr Glu Ile Pro Glu Ala Gln Ile His Glu Gly Phe Gln Glu Leu Leu Arg Thr Leu Asn Gln>

320           330           340           350           360           370
     g   c                 c                 c   g   c             g tcc        c       c
CCA GAC AGC CAG CTC CAG CTG ACC ACC GGC AAT GGC CTG TTC CTC AGC GAG GGC CTG AAG CTA
Pro Asp Ser Gln Leu Gln Leu Thr Thr Gly Asn Gly Leu Phe Leu Ser Glu Gly Leu Lys Leu>

380           390           400           410           420           430           440
     c             c   c         c   g   g       c c             c   g   g         c
GTG GAT AAG TTT TTG GAG GAT GTT AAA AAG TTG TAC CAC TCA GAA GCC TTC ACT GTC AAC TTC
Val Asp Lys Phe Leu Glu Asp Val Lys Lys Leu Tyr His Ser Glu Ala Phe Thr Val Asn Phe>

450           460           470           480           490           500
                      g             g                 c         c             g c g c g
GGG GAC ACC GAA GAG GCC AAG AAA CAG ATC AAC GAT TAC GTG GAG AAG GGT ACT CAA GGG AAA
Gly Asp Thr Glu Glu Ala Lys Lys Gln Ile Asn Asp Tyr Val Glu Lys Gly Thr Gln Gly Lys>

510           520           530           540           550           560
     c             c c           a t g         g         c   c   c   g   c   c
ATT GTG GAT TTG GTC AAG GAG CTT GAC AGA GAC ACA GTT TTT GCT CTG GTG AAT TAC ATC TTC
Ile Val Asp Leu Val Lys Glu Leu Asp Arg Asp Thr Val Phe Ala Leu Val Asn Tyr Ile Phe>

570           580           590           600           610           620           630
     c   g         g           c c   g   c   g                         g                 c
TTT AAA GGC AAA TGG GAG AGA CCC TTT GAA GTC AAG GAC ACC GAG GAA GAG GAC TTC CAC GTG
Phe Lys Gly Lys Trp Glu Arg Pro Phe Glu Val Lys Asp Thr Glu Glu Glu Asp Phe His Val>
```

Fig. 1A

```
           640           650           660           670           680           690
             c             c         c     g                   a g c c                 c
GAC CAG GTG ACC ACC GTG AAG GTG CCT ATG ATG AAG CGT TTA GGC ATG TTT AAC ATC CAG CAC
Asp Gln Val Thr Thr Val Lys Val Pro Met Met Lys Arg Leu Gly Met Phe Asn Ile Gln His>

700           710           720           730           740           750
             c             c                     c   c             g           g   c
TGT AAG AAG CTG TCC AGC TGG GTG CTG CTG ATG AAA TAC CTG GGC AAT GCC ACC GCC ATC TTC
Cys Lys Lys Leu Ser Ser Trp Val Leu Leu Met Lys Tyr Leu Gly Asn Ala Thr Ala Ile Phe>

760           770           780           790           800           810
                     g   c     c   g   c                 g   c   g   g             c           g
TTC CTG CCT GAT GAG GGG AAA CTA CAG CAC CTG GAA AAT GAA CTC ACC CAC GAT ATC ATC ACC
Phe Leu Pro Asp Glu Gly Lys Leu Gln His Leu Glu Asn Glu Leu Thr His Asp Ile Ile Thr>

820           830           840           850           860           870           880
                 g   c     g       g c c       c       c c       c c c       g       g           a g c     c     c
AAG TTC CTG GAA AAT GAA GAC AGA AGG TCT GCC AGC TTA CAT TTA CCC AAA CTG TCC ATT ACT
Lys Phe Leu Glu Asn Glu Asp Arg Arg Ser Ala Ser Leu His Leu Pro Lys Leu Ser Ile Thr>

890           900           910           920           930           940
   c   g   c   c                     g             c   g                 g                     c   c
GGA ACC TAT GAT CTG AAG AGC GTC CTG GGT CAA CTG GGC ATC ACT AAG GTC TTC AGC AAT GGG
Gly Thr Tyr Asp Leu Lys Ser Val Leu Gly Gln Leu Gly Ile Thr Lys Val Phe Ser Asn Gly>

950           960           970           980           990          1000
   g                     c   g   g             c                                             c         g
GCT GAC CTC TCC GGG GTC ACA GAG GAG GCA CCC CTG AAb CTC TCC AAG GCC GTG CAT AAG GCT
Ala Asp Leu Ser Gly Val Thr Glu Glu Ala Pro Leu Lys Leu Ser Lys Ala Val His Lys Ala>

1010          1020          1030          1040          1050          1060          1070
         c   g                 g             g                 c                   c c g               c
GTG CTG ACC ATC GAC GAG AAA GGG ACT GAA GCT GCT GGG GCC ATG TTT TTA GAG GCC ATA CCC
Val Leu Thr Ile Asp Glu Lys Gly Thr Glu Ala Ala Gly Ala Met Phe Leu Glu Ala Ile Pro>

1080          1090          1100          1110          1120          1130
         c             g                             g       c       c g       c   g   g   c
ATG TCT ATC CCC CCC GAG GTC AAG TTC AAC AAA CCC TTT GTC TTC TTA ATG ATT GAA CAA AAT
Met Ser Ile Pro Pro Glu Val Lys Phe Asn Lys Pro Phe Val Phe Leu Met Ile Glu Gln Asn>

1140          1150          1160          1170          1180
   g       a g c                     g   g   c     c   c           g     g   g     g
ACC AAG TCT CCC CTC TTC ATG GGA AAA GTG GTG AAT CCC ACC CAA AAA TAA
Thr Lys Ser Pro Leu Phe Met Gly Lys Val Val Asn Pro Thr Gln Lys ***>
```

Fig. 1B

```
                                        NotI
                                        |3530        3540
                                        |   *    *    *
                                        GCGGC CGCTCACTAT 3550       3560       3570       3580       3590
          *    *    *    *    *    *    *    *    *    *
      CGAACACGGT TTCAGCTTAC ACAGAT ATG AAG AAC ACC TCC TCC CTC TGC CTC
                                   Met Lys Asn Thr Ser Ser Leu Cys Leu 3600       3610       3620       3630       3640
          *    *    *    *    *    *    *    *    *    *
      CTG CTG CTC GTG GTC CTC TGC TCC CTG ACC TGC AAC AGC GGC CAG GCC
      Leu Leu Leu Val Val Leu Cys Ser Leu Thr Cys Asn Ser Gly Gln Ala

XhoI   XbaI
                   |      |
                   |      |           RAmy3D 3'UTR
         3650     3660   |  3670     3680  |  3690       3700
          *    *   * | *  |*    *    *   * |  *    *    *    *
      AGCTCCATG GCCGTGGCTC GAGTCTAGAC GCGTCCCGGG GGGGCGGCAC CTATAGCGGG
```

| Digest p3d v2.1 and p3d v2.1.1 with NotI and XhoI

Digest Codon-optimized AAT with NotI and XhoI

| Ligation to form p3D AAT v2.1 and p3D AAT v2.1.1

PRODUCTION OF α₁-ANTITRYPSIN IN PLANTS

This application claims the priority of U.S. Provisional Application No. 60/037,991 filed Feb. 13, 1997, which is incorporated herein by reference.

FIELD OF THE INVENTION

The present invention relates to a method for the producing recombinant $\alpha_1$-antitrypsin (AAT) in plants, to a codon-optimized coding sequence for expression of AAT in plants, and to a plant-glycosylated AAT composition.

BACKGROUND OF THE INVENTION

Human $\alpha_1$-antitrypsin (AAT) is a monomer with a molecular weight of about 52 Kd. Normal AAT contains 394 residues, with three complex oligosaccharide units exposed to the surface of the molecule, linked to asparagines 46, 83, and 247 (Carrell, et al., Nature 298:329 (1982).

AAT is the major plasma proteinase inhibitor whose primary function is to control the proteolytic activity of trypsin, elastase, and chymotrypsin in plasma. In particular, the protein is a potent inhibitor of neutrophile elastase, and a deficiency of AAT has been observed in a number of patients with chronic emphysema of the lungs. A proportion of individuals with serum deficiency of AAT may progress to cirrhosis and liver failure (e.g., Wu, et al., *BioEssays* 13(4):163 (1991).

Because of the key role of AAT as an elastase inhibitor, and because of the prevalence of genetic diseases resulting in deficient serum levels of AAT, there has been an active interest in recombinant synthesis of AAT, for human therapeutic use. To date, this approach has not been satisfactory for AAT produced by microbial recombinant methods, because of a short effective serum halflife of the recombinant protein. Methods for making AAT using mammalian cell culture or transgenic animals, while expected to produce a more active AAT, by virtue of a more human glycosylation pattern, are relatively expensive, and to date, have limited the available supply of glycosylated AAT.

It would therefore be useful to provide a method for inexpensive production of glycosylated, therapeutically effective AAT.

SUMMARY OF THE INVENTION

In one aspect, the invention provides a method for producing a stable, glycosylated AAT in plant cells. The method includes obtaining monocot cells transformed with heterologous nucleic acid containing a coding sequence for AAT under the control of a monocot promoter, which is inducible by addition or depletion of a small molecule, and a signal peptide which allows for secretion of AAT from the transformed cells. The transformed cells are cultivated under conditions effective to induce the promoter, thereby promoting expression and secretion of AAT into the cell culture media.

The coding sequence for the protein may be matched for the host plant, for example, for rice cells, where the coding sequence is identified by SEQ ID NO:3.

In one general embodiment, the transformed cells are rice or barley callus cells, and the cells are cultivated in a low-sugar or sugar depleted media. Suitable promoters include the α-amylase rice RAmy3D or RAmy3E promoter.

In another general embodiment, the transformed cells are rice or barley aleurone cells, and the cultivating is carried out in germinating seeds. One suitable promoter is the rice α-amylase RAmy1A promoter, where seed germination is induced by gibberellic acid.

In a related aspect, the invention includes a stable, glycosylated form of AAT having the sequence identified by SEQ ID NO:1, or a sequence homologous thereto, and the glycosylation pattern produced by expression of the enzyme in a monocotyledonous plant.

Also forming part of the invention is a DNA coding sequence for expression of AAT in monocot plants, having the sequence identified by SEQ ID NO:3.

In another aspect the invention includes a method of enhancing the expression level of AAT in a monocot plant. The method includes determining, for each amino acid, the maximum-frequency codon present in a representative set of genes from said plant, and replacing substantially each codon in a native AAT gene with the determined maximum-frequency codon.

These and other objects and features of the invention will be more fully understood when the following detailed description of the invention is read in conjunction with the accompanying drawings.

BRIEF DESCRIPTION OF THE FIGURES

FIG. 1 illustrates the AAT coding (upper case) and amino acid sequences, identified herein as SEQ ID NO:2 and SEQ ID NO:1, respectively, and a codon-optimized AAT (lower case) coding sequence, identified herein as SEQ ID NO:3;

FIGS. 3A–3E illustrate the construction of an exemplary transformation vector for use in transforming a monocot plant, for AAT production in cell culture in accordance with one embodiment of the invention (AAT codon-optimized coding sequence under control of 3D promoter);

BRIEF DESCRIPTION OF THE SEQUENCES

Figure 2A:
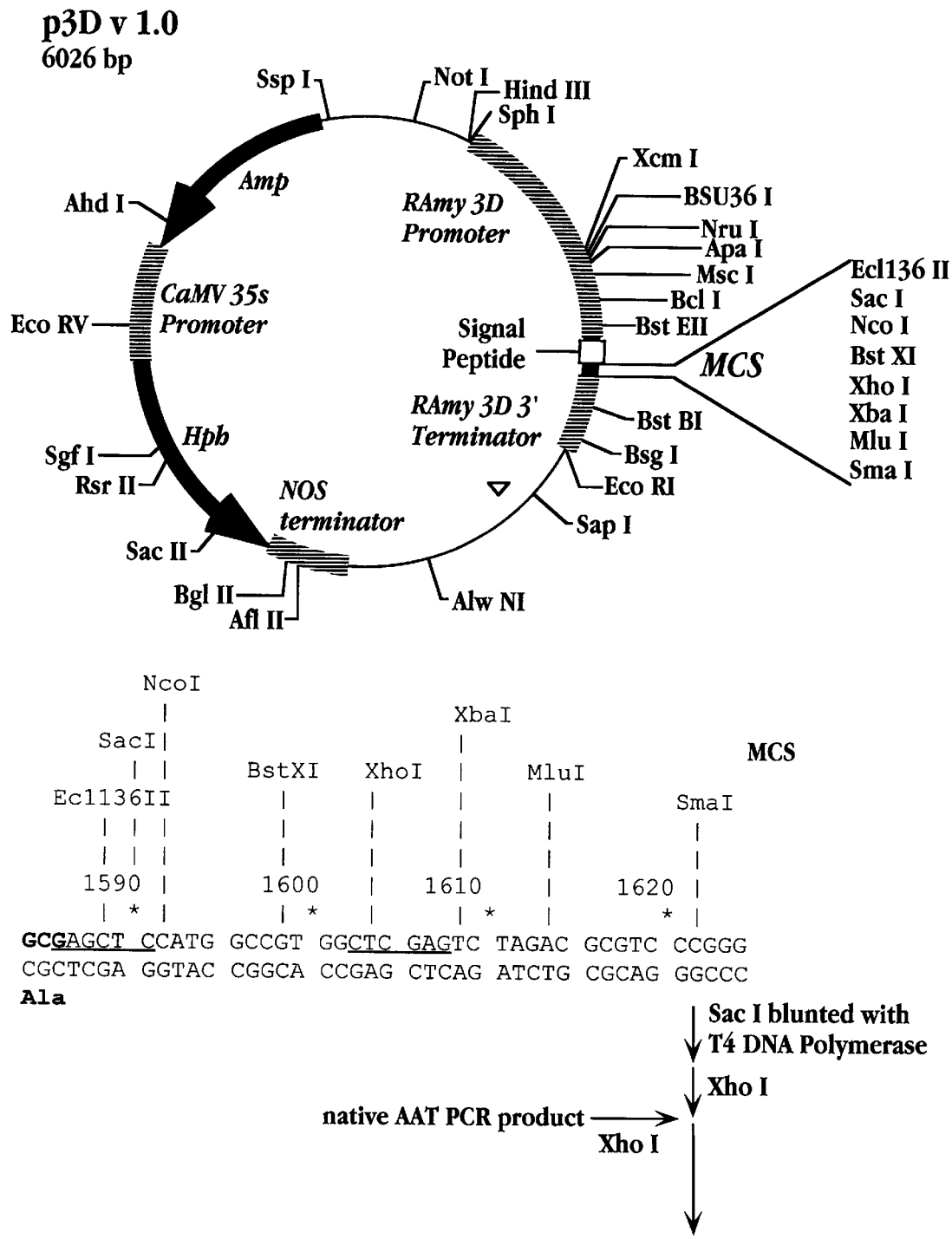
FIGS. 2A and 2B illustrate the construction of an exemplary transformation vector for use in transforming a monocot plant, for AAT production in cell culture in accordance with one embodiment of the invention (AAT native coding sequence under control of 3D promoter)

SEQ ID NO:1 is the amino acid sequence of mature AAT;

SEQ ID NO:2 is the native nucleotide sequence encoding mature AAT;

SEQ ID NO:3 is a codon-optimized nucleotide sequence encoding mature AAT;

SEQ ID NO:4 is the amino acid sequence of the RAmy3D signal peptide;

SEQ ID NO:5 is the amino acid sequence of the RAmy1A signal peptide;

SEQ ID NO:6 is a codon-optimized sequence encoding the 3D signal peptide-mature AAT fusion protein;

SEQ ID NO:7 is the N-terminal sequence of mature $\alpha_1$-antitrypsin produced in accordance with the invention.

SEQ ID NO:8 is an oligonucleotide used to prepare the intermediate p3DProSig construct of Example 1;

SEQ ID NO:9 is the complement of SEQ ID NO:8;

SEQ ID NO:10 is an oligonucleotide used to prepare the intermediate p3DProSigENDlink construct of Example 1;

SEQ ID NO:11 is the complement of SEQ ID NO:10;

SEQ ID NO:12 is one of six oligonucleotides used to prepare the intermediate p1AProSig construct of Example 1;

SEQ ID NO:13 is one of six oligonucleotides used to prepare the intermediate p1AProSig construct of Example 1;

SEQ ID NO:14 is one of six oligonucleotides used to prepare the intermediate p1AProSig construct of Example 1;

SEQ ID NO:15 is one of six oligonucleotides used to prepare the intermediate p1AProSig construct of Example 1;

SEQ ID NO:16 is one of six oligonucleotides used to prepare the intermediate p1AProSig construct of Example 1;

SEQ ID NO:17 is one of six oligonucleotides used to prepare the intermediate p1AProSig construct of Example 1;

SEQ ID NO:18 is the N-terminal primer used to PCR-amplify the AAT coding sequence according to Example 1;

SEQ ID NO:19 is the C-terminal primer used to PCR-amplify the AAT coding sequence according to Example 1;

SEQ ID NO:20 is the mutagenic oligonucleotide used to introduce a NotI site into p3Dv2.0 according to Example 1;

SEQ ID NO:21 is an oligonucleotide used to prepare the p3D-AAT2.1.1 expression vector according to Example 1; and SEQ ID NO:22 is an oligonucleotide used to prepare the p3D-AAT2.1.1 expression vector according to Example 1.

DETAILED DESCRIPTION OF THE INVENTION

I. Definitions

The terms below have the following meaning, unless indicated otherwise in the specification. "Cell culture" refers to cells and cell clusters, typically callus cells, growing on or suspended in a suitable growth medium.

"Inducible" means a promoter that is upregulated by the presence or absence of a small molecules. It includes both indirect and direct inducement.

"Germination" refers to the breaking of dormancy in a seed and the resumption of metabolic activity in the seed, including the production of enzymes effective to break down starches in the seed endosperm.

"Inducible during germination" refers to promoters which are substantially silent but not totally silent prior to germination but are turned on substantially (greater than 25%) during germination and development in the seed. Examples of promoters that are inducible during germination are presented below.

"Small molecules", in the context of promoter induction, are typically small organic or bioorganic molecules less than about 1 kilodalton. Examples of such small molecules include sugars, sugar-derivatives (including phosphate derivatives), and plant hormones (such as, gibberellic or absissic acid).

"Specifically regulatable" refers to the ability of a small molecule to preferentially affect transcription from one promoter or group of promoters (e.g., the α-amylase gene family), as opposed to non-specific effects, such as, enhancement or reduction of global transcription within a cell by a small molecule.

"Heterologous DNA" or "foreign DNA" refers to DNA which has been introduced into plant cells from another source, or which is from a plant source, including the same plant source, but which is under the control of a promoter or terminator that does not normally regulate expression of the heterologous DNA.

"Heterologous protein" is a protein, including a polypeptide, encoded by a heterologous DNA.

A "transcription regulatory region" or "promoter" refers to nucleic acid sequences that influence and/or promote initiation of transcription. Promoters are typically considered to include regulatory regions, such as enhancer or inducer elements.

A "chimeric gene," in the context of the present invention, typically comprises a promoter sequence operably linked to DNA sequence that encodes AAT or a another gene product, e.g., a selectable marker gene. A chimeric gene may also contain further transcription regulatory elements, such as transcription termination signals, as well as translation regulatory signals, such as, termination codons.

"Operably linked" refers to components of a chimeric gene or an expression cassette that function as a unit to express a heterologous protein. For example, a promoter operably linked to a heterologous DNA, which encodes a protein, promotes the production of functional mRNA corresponding to the heterologous DNA.

A "product" encoded by a DNA molecule includes, for example, RNA molecules and polypeptides.

Two nucleotide sequences are considered to be "functionally homologous" if they hybridize with one another under moderately stringent conditions, i.e. 0.1% SSC at room temperature. Typically, two homologous nucleotide sequences are greater than or equal to about 60% identical when optimally aligned using the ALIGN program (Dayhoff, in *ATLAS OF PROTEIN SEQUENCE AND STRUCTURE* Vol. 5, National Biomedical Research Foundation, pp. 101–110, and Supplement 2 to this volume, pp. 1–10. (1972)).

Two amino acid sequences are considered "homologous", or "homologs", if their amino acids are greater than or equal to about 80% identical when optimally aligned using the ALIGN program mentioned above.

"Removal" in the context of a metabolite includes both physical removal as by washing and the depletion of the metabolite through the absorption and metabolizing of the metabolite by the cells.

"Substantially isolated" is used in several contexts and typically refers to the at least partial purification of a protein or polypeptide away from unrelated or contaminating components. Methods and procedures for the isolation or purification of proteins or polypeptides are known in the art.

"Stably transformed" as used herein refers to a barley cell or plant that has foreign nucleic acid integrated into its genome which is maintained through at least three or more generations.

"$\alpha_1$-antitrypsin" or "AAT" refers to the protease inhibitor which has an amino acid sequence substantially identical or homologous to AAT protein identified by SEQ ID NO:1.

"Codon optimization" refers to changes in the coding sequence of a gene to replace native codons with those corresponding to optimal codons in the host plant.

A DNA sequence is "derived from" a gene, such as a rice or barley α-amylase gene, if it corresponds in sequence to a segment or region of that gene. Segments of genes which may be derived from a gene include the promoter region, the 5' untranslated region, and the 3' untranslated region of the gene.

II. Transformed Plant Cells

The plants used in the process of the present invention are derived from monocots, particularly the members of the taxonomic family known as the Gramineae. This family includes all members of the grass family of which the edible varieties are known as cereals. The cereals include a wide variety of species such as wheat (Triticum sps.), rice (Oryza sps.) barley (Hordeum sps.) oats, (Avena sps.) rye (Secale sps.), corn (Zea sps.) and millet (Pennisettum sps.). In the present invention, preferred family members are rice and barley.

Plant cells or tissues derived from the members of the family are transformed with expression constructs (i.e., plasmid DNA into which the gene of interest has been inserted) using a variety of standard techniques (e.g., electroporation, protoplast fusion or microparticle bombardment). The expression construct includes a transcription regulatory region (promoter) whose transcription is specifically upregulated by the presence of absence of a small molecule, such as the reduction or depletion of sugar, e.g., sucrose, in culture medium, or in plant tissues, e.g., germinating seeds. In the present invention, particle bombardment is the preferred transformation procedure.

The construct also includes a gene encoding AAT in a form suitable for secretion from plant cells. The gene encoding the recombinant AAT is placed under the control of a metabolically regulated promoter. Metabolically regulated promoters are those in which mRNA synthesis or transcription, is repressed or upregulated by a small metabolite or hormone molecule, such as the rice RAmy3D and RAmy3E promoters, which are upregulated by sugar-depletion in cell culture. For protein production in germinating seeds from regenerated transgenic plants, a preferred promoter is the RAmy1A promoter, which is up-regulated by gibberellic acid during seed germination. The expression construct also utilizes additional regulatory DNA sequences e.g., preferred codons, termination sequences, to promote efficient translation of AAT, as will be described.

A. Plant Expression Vector

Expression vectors for use in the present invention comprise a chimeric gene (or expression cassette), designed for operation in plants, with companion sequences upstream and downstream from the expression cassette. The companion sequences will be of plasmid or viral origin and provide necessary characteristics to the vector to permit the vectors to move DNA from bacteria to the desired plant host. Suitable transformation vectors are described in related application PCT WO 95/14099, published May 25, 1995, which is incorporated by reference herein. Suitable components of the expression vector, including an inducible promoter, a signal sequence, coding sequence for AAT, and suitable termination sequences are discussed below. One exemplary vector is the p3D(AAT)v1.0 vector illustrated in FIGS. 2A and 2B.

A1. Promoters

The transcription regulatory or promoter region is chosen to be regulated in a manner allowing for induction under selected cultivation conditions, e.g., sugar depletion in culture or water uptake followed by gibberellic acid production in germinating seeds. Suitable promoters, and their method of selection are detailed in above-cited PCT application WO 95/14099. Examples of such promoters include those that transcribe the cereal α-amylase genes and sucrose synthase genes, and are repressed or induced by small molecules, like sugars, sugar depletion or phytohormones such as gibberellic acid or absissic acid. Representative promoters include the promoters from the rice α-amylase RAmy1A, RAmy1B, RAmy2A, RAmy3A, RAmy3B, RAmy3C, RAmy3D, and RAmy3E genes, and from the pM/C, gKAmy141, gKAmy155, Amy32b, and HV18 barley α-amylase genes.

These promoters are described, for example, in *ADVANCES IN PLANT BIOTECHNOLOGY* Ryu, D. D. Y., et al, Eds., Elsevier, Amsterdam, 1994, p.37, and references cited therein; Other suitable vectors include the sucrose synthase and sucrose-6-phosphate-synthetase (SPS) promoters from rice and barley.

A preferred promoter for expression in germinating seeds is the rice α-amylase RAmy1A promoter, which is upregulated by gibberellic acid. Preferred promoters for expression in cell culture are the rice α-amylase RAmy3D and RAmy3E promoters which are strongly upregulated by sugar depletion in the culture. These promoters are also active during seed germination.

A2. Signal Sequences

In addition to encoding the protein of interest, the expression cassette's chimeric gene encodes a signal peptide that allows processing and translocation of the protein, as appropriate. Suitable signal sequences are described in above-referenced PCT application WO 95/14099. Preferred signal sequences are those shown in SEQ ID NO:4 and SEQ ID NO:5, from derived from the RAmy3D promoter and RAmy1A promoter, respectively. A plant signal sequence is placed in frame with a heterologous nucleic acid encoding a peptide or protein such that signal peptidase cleavage occurs precisely at the start of the mature peptide.

A3. Naturally-Occurring AAT Coding Sequences

Normal human AAT is composed of 394 amino acids, having the sequence shown FIG. 1, and identified herein as SEQ ID NO:1. The protein has glycosylation sites at asparagines 46, 83 and 247. The figure also shows the corresponding 1182 base DNA coding sequence (in CAPS), identified herein as SEQ ID NO:2. The single copy gene for human AAT is 12.2 kb in length and contains seven exons separated by six non-coding exons (Perlino, et al., *EMBO J.*, 6:2767 (1987).

A4. Codon-Optimized AAT Coding Sequences

In accordance with one aspect of the invention, it has been discovered that a severalfold enhancement of expression level can be achieved in plant cell culture by modifying the native coding sequence of a heterologous gene by contain predominantly or exclusively, highest-frequency codons found in the plant cell host.

The method will be illustrated for expression of a heterologous gene in rice plant cells, it being recognized that the method is generally applicable to any monocot. As a first step, a representative set of known coding gene sequence from rice is assembled. The sequences are then analyzed for codon frequency for each amino acid, and the most frequent codon is selected for each amino acid. This approach differs from earlier reported codon matching methods, in which more than one frequent codon is selected for at least some of the amino acids. The optimal codons selected in this manner for rice and barley are shown in Table 1.

TABLE 1

| Amino Acid | Rice Preferred Codon | Barley Preferred Codon |
|---|---|---|
| Ala A | GCC | |
| Arg R | CGC | |
| Asn N | AAC | |
| Asp D | GAC | |
| Cys C | UGC | |
| Gln Q | CAG | |
| Glu E | GAG | |
| Gly G | GGC | |
| His H | CAC | |
| Ile I | AUC | |

TABLE 1-continued

| Amino Acid | Rice Preferred Codon | Barley Preferred Codon |
|---|---|---|
| Leu L | CUC | |
| Lys K | AAG | |
| Phe F | UUC | |
| Pro P | CCG | CCC |
| Ser S | AGC | UCC |
| Thr T | ACC | |
| Tyr Y | UAC | |
| Val V | GUC | GUG |
| stop | UAA | UGA |

The coding sequence for AAT was then modified to replace non-optimal codons with the corresponding codons from Table 1. The resulting nucleic acid sequence is identified as SEQ ID NO:3, and is shown in lower case in FIG. 1.

A5. Transcription and Translation Terminators

The expression cassette or chimeric genes in the transforming vector typically have a transcriptional termination region at the opposite end from the transcription initiation regulatory region. The transcriptional termination region may normally be associated with the transcriptional initiation region or from a different gene. The transcriptional termination region may be selected, particularly for stability of the mRNA to enhance expression. Illustrative transcriptional termination regions include the NOS terminator from Agrobacterium Ti plasmid and the rice α-amylase terminator.

Polyadenylation tails, Alber and Kawasaki, *Mol. and Appl. Genet.* 1:419–434 (1982) are also commonly added to the expression cassette to optimize high levels of transcription and proper transcription termination, respectively. Polyadenylation sequences include, but are not limited to, the Agrobacterium octopine synthetase signal, Gielen, et al., *EMBO J.* 3:835–846 (1984) or the nopaline synthase of the same species Depicker, et al., *Mol. Appl. Genet.* 1:561–573 (1982).

Since the ultimate expression of the AAT will be in a eukaryotic cell (in this case, a member of the grass family), it is desirable to determine whether any portion of the cloned gene contains sequences which will be processed out as introns by the host's splicing machinery. If so, site-directed mutagenesis of the "intron" region may be conducted to prevent losing a portion of the genetic message as a false intron code, Reed and Maniatis, *Cell* 41:95–105, 1985.

A6. Construction of Transforming Vector

Vectors containing a chimeric gene of the present invention may also include selectable markers for use in plant cells (such as the nptII kanamycin resistance gene, for selection in kanamycin-containing or the phosphinothricin acetyltransferase gene, for selection in medium containing phosphinothricin (PPT).

The vectors may also include sequences that allow their selection and propagation in a secondary host, such as, sequences containing an origin of replication and a selectable marker such as antibiotic or herbicide resistance genes, e.g., HPH (Hagio et al., *Plant Cell Reports* 14:329 (1995) and van der Elzer *Plant Mol. Biol.* 5:299–302 (1985)). Typical secondary hosts include bacteria and yeast. In one embodiment, the secondary host is *Escherichia coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

Figure 2B:
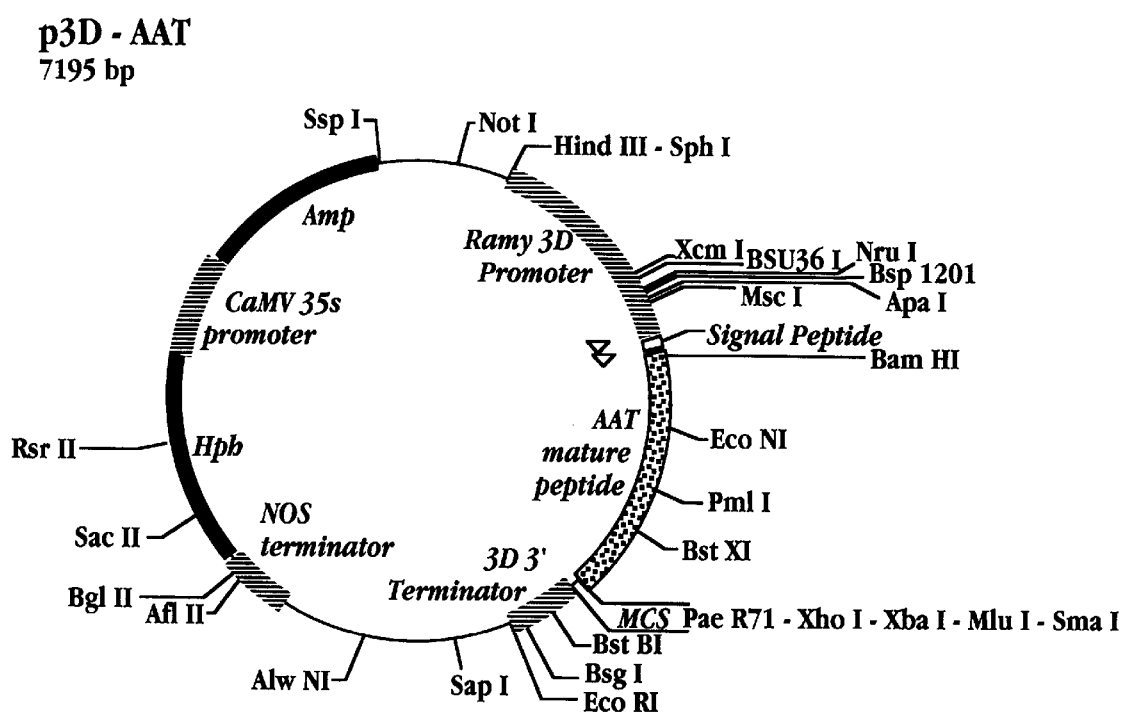

FIGS. 2A ad 2B show steps in construction of an exemplary transformation vector for use in transforming rice plant cells capable of expressing mature AAT in plant cell culture, where the vector in FIG. 2B contains native AAT coding sequence. Details of the vector construction are given in Example 1. Briefly the p3Dv1.0 plasmid shown in FIG. 2A contains the RAmy3D promoter, a multiple cloning site (MCS) and a RAmy3D terminator sequence. The vector is cut at the MCS with SacI, blunted with T4 DNA polymerase, and then cut with XhoI. Native AAT or codon-optimized sequence from the sources indicated in Example 1 is cut with XhoI, and ligated into the cut p3D vector, to form the corresponding p3D-AAT plasmid with native or codon-optimized AAT sequence in-frame with the signal sequence from the RAmy3D promoter.

Figure 3A:
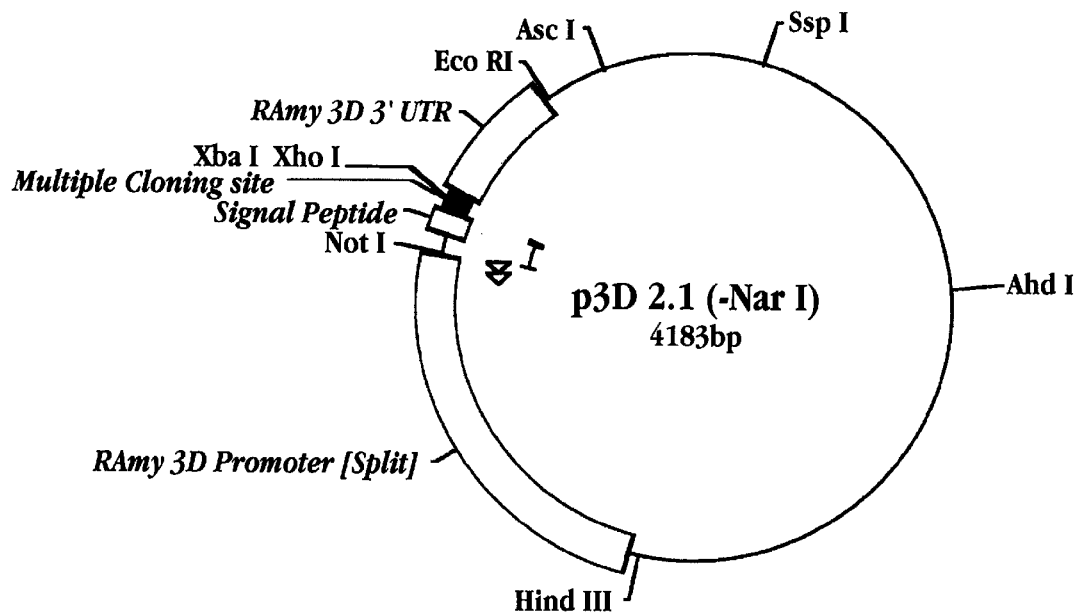
Figure 3B:
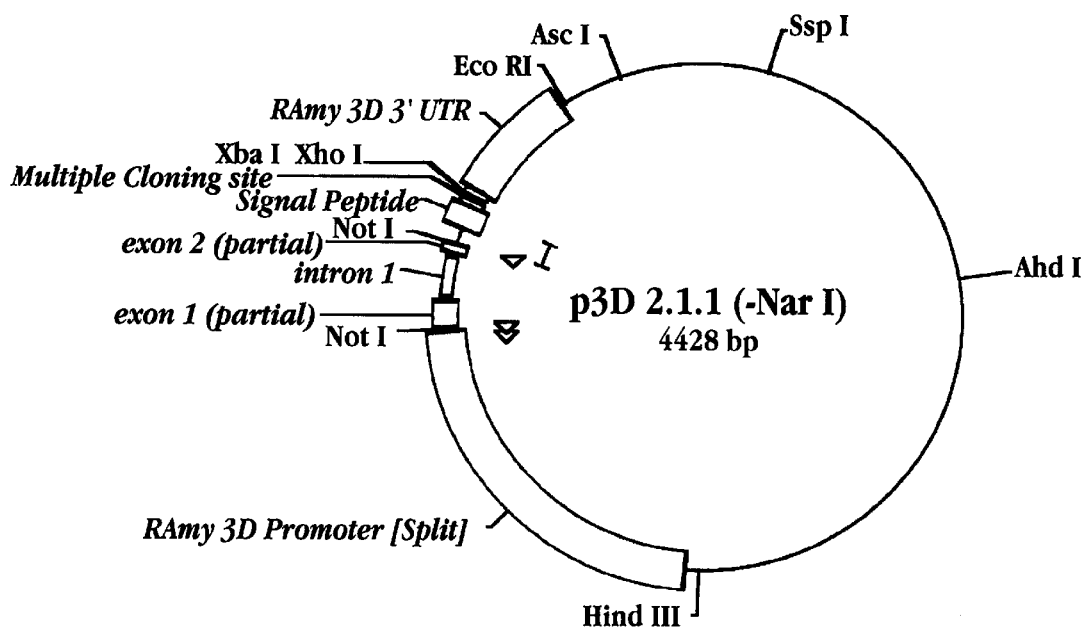
Figure 3D:
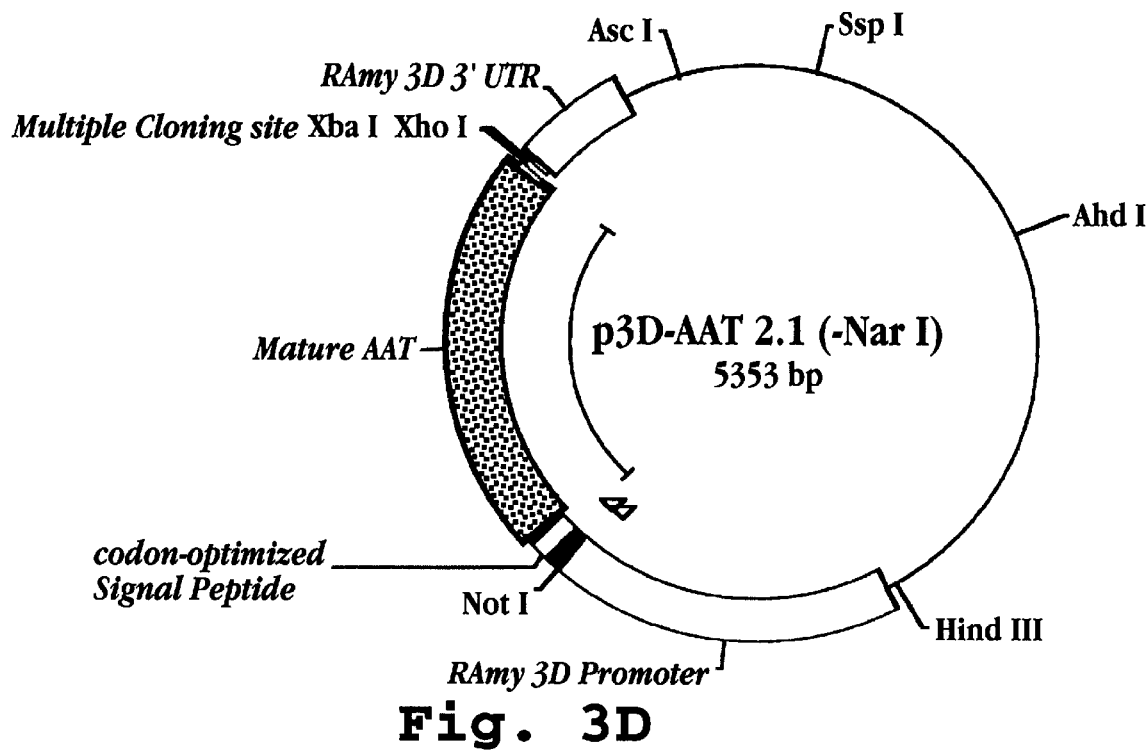
Figure 3E:
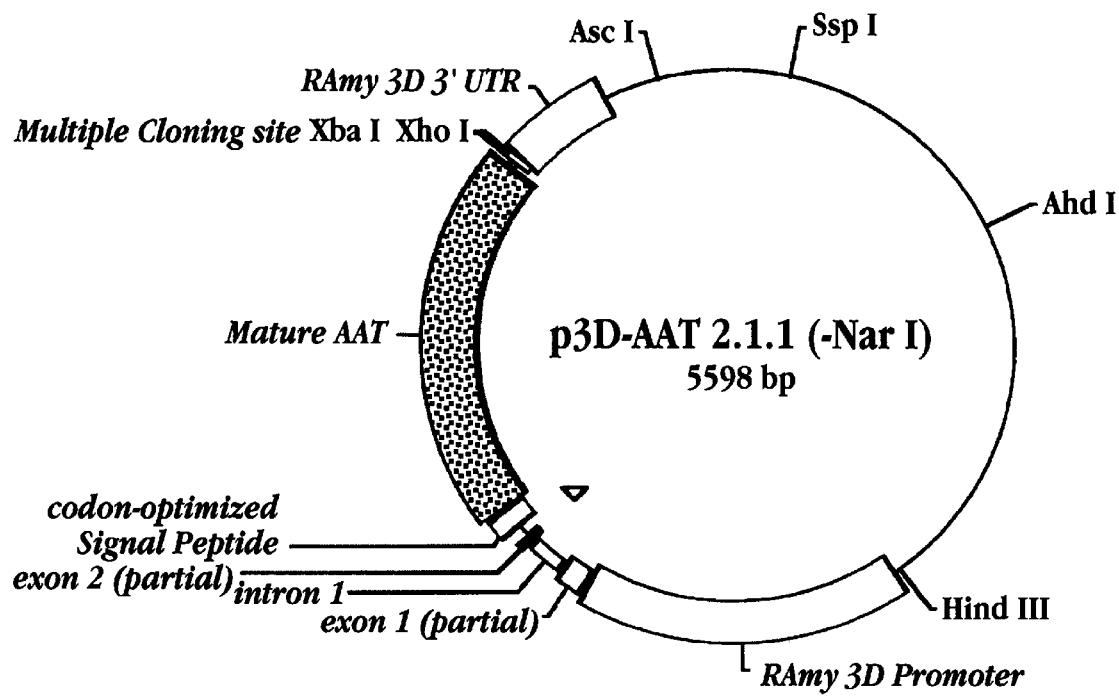

In the vector construction scheme shown in FIGS. 3A–3C, either of two starting plasmids, identified as p3D 2.1 and p3D 2.1.1, each of which contains the RAmy3D promoter, the RAmy3D signal peptide, a multiple cloning site (MCS) and a RAmy3D 3' UTR terminator sequence. Each vector is cut at the MCS with NotI and XhoI. Codon-optimized AAT sequence from the sources indicated in Example 1 is cut with NotI and XhoI, and ligated into the cut p3D vector, to form the corresponding p3D-AAT 2.1 or p3D AAT 2.1.1. plasmids with codon-optimized AAT sequence in-frame with the signal sequence from the RAmy3D promoter.

The vectors described above are suitable for use in a method of AAT production in cell culture, where the RAmy3D promoter is induced by sugar depletion in cell culture medium. Other promoters may be selected for other applications, as indicated above. For example, for AAT expression in germinating seeds, the AAT coding sequence may be placed under the control of the rice α-amylase RAmy1A promoter, which is inducible by gibberellic acid during seed germination. Examples of other suitable promoters, such as Amy64 and Amy32B, are given above.

B. Transformation of Plant Cells

Various methods for direct or vectored transformation of plant cells, e.g., plant protoplast cells, have been described, e.g., in above-cited PCT application WO 95/14099. As noted in that reference, promoters directing expression of selectable markers used for plant transformation (e.g., nptII) should operate effectively in plant hosts. One such promoter is the nos promoter from native Ti plasmids, Herrera-Estrella, et al., *Nature* 303:209–213 (1983). Others include the 35S and 19S promoters of cauliflower mosaic virus, Odell, et al., *Nature* 313:810–812 (1985), and the 2' promoter, Velten, et al., *EMBO J.* 3:2723–2730 (1984).

In one preferred embodiment, the embryo and endosperm of mature seeds are removed to exposed scutulum tissue cells. The cells may be transformed by DNA bombardment or injection, or by vectored transformation, e.g., by Agrobacterium infection after bombarding the scuteller cells with microparticles to make them susceptible to Agrobacterium infection (Bidney et al. *Plant Mol. Biol.* 18:301–313 (1992)).

One preferred transformation follows the methods detailed generally in Sivamani, E. et al., *Plant Cell Reports*

15:465 (1996); Zhang, S., et al., *Plant Cell Reports* 15:465 (1996); and Li, L., et al., *Plant Cell Reports* 12:250 (1993). Briefly, rice seeds are sterilized by standard methods, and callus induction from the seeds is carried out on MB media with 2,4D. During a first incubation period, callus tissue forms around the embryo of the seed. By the end of the incubation period, (e.g., 14 days at 28° C.) the calli are about 0.25 to 0.5 cm in diameter. Callus mass is then detached from the seed, and placed on fresh NB media, and incubated again for about 14 days at 28° C. After the second incubation period, satellite calli developed around the original "mother" callus mass. These satellite calli were slightly smaller, more compact and defined than the original tissue. It was these calli were transferred to fresh media. The "mother" calli was not transferred. The goal was to select only the strongest, most vigorous growing tissue for further culture.

Calli to be bombarded are selected from 14 day old subcultures. The size, shape, color and density are all important in selecting calli in the optimal physiological condition for transformation. The calli should be between 0.8 and 1.1 mm in diameter. The calli should appear as spherical masses with a rough exterior.

Transformation is by particle bombardment, as detailed in the references cited above. After the transformation steps, the cells are typically grown under conditions that permit expression of the selectable marker gene. In a preferred embodiment, the selectable marker gene is HPH. It is preferred to culture the transformed cells under multiple rounds of selection to produce a uniformly, stable transformed cell line.

III. Cell Culture Production of Mature, Glycosylated AAT

Transgenic cells, typically callus cells are cultured under conditions that favor plant cell growth, until the cells reach a desired cell density, then under conditions that favor expression of AAT under the control of the given promoter. Exemplary cell culture conditions are disclosed in Example 2. In a preferred embodiment, the culture medium contains a phosphate buffer, e.g., the 20 mM phosphate buffer, pH 6.8 described in Example 2, to reduce AAT degradation catalyzed by metals. Alternatively, or in addition, a metal chelating agent, such as EDTA, may be added to the medium.

Figure 4:
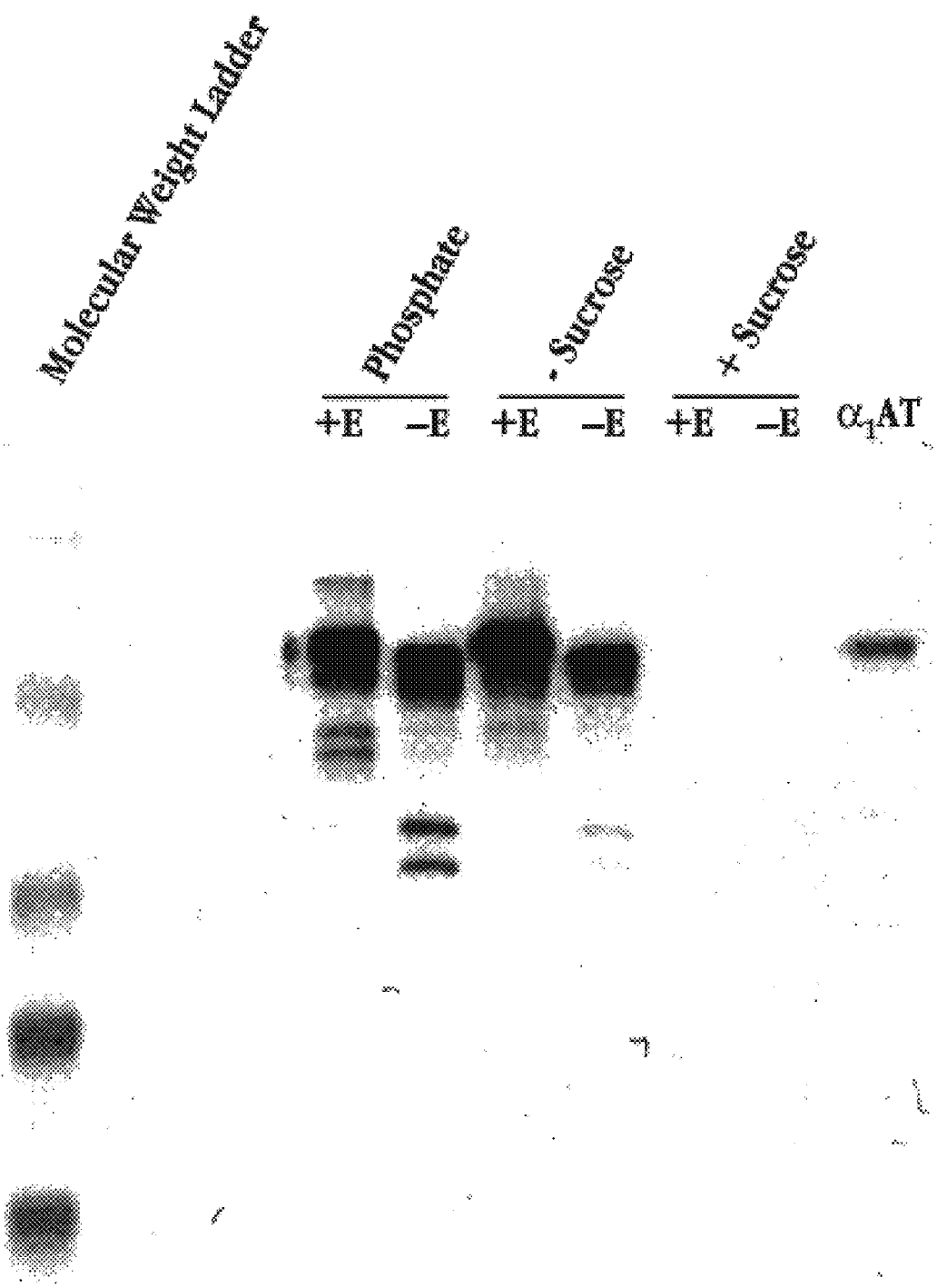
FIG. 4 illustrates factors in the metabolic regulation of AAT production in rice cell culture.

Following the cell culture method detailed in Example 2, cell culture media was partially purified and the fraction containing AAT was analyzed by Western blot, as shown in FIG. 4. The first two lanes ("phosphate") show AAT bands both in the presence and absence of elastase ("+E" and "−E"), where the higher molecular weight bands in the presence of elastase correspond roughly to a 58–59 kdal AAT/elastase complex. Also as seen in the figure, expression was high in the absence of sucrose, but nearly undetectable in the presence of sucrose.

Figure 5:
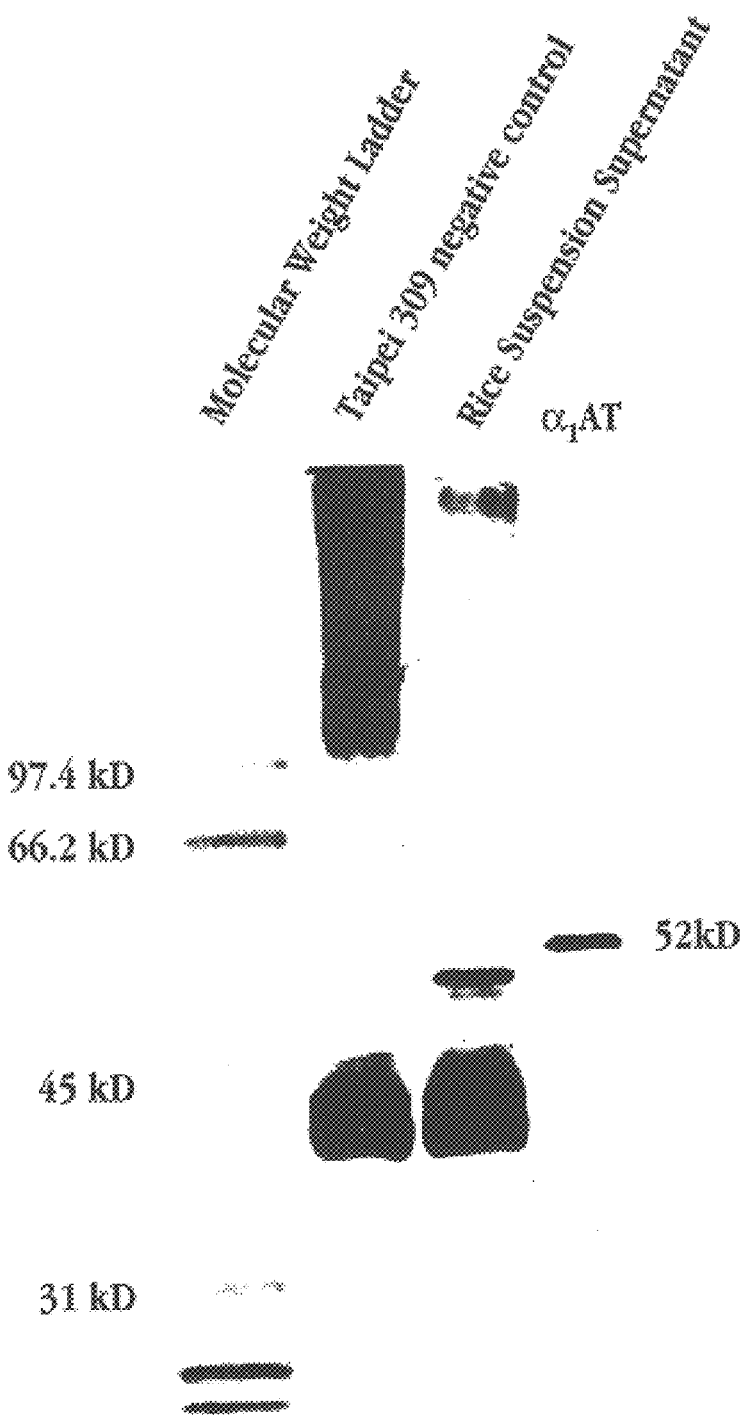
FIG. 5 shows immunodetection of AAT using antibody raised against the C-terminal region of AAT.

To ascertain the degree of glycosylation (as determined by apparent molecular weight by SDS-PAGE) the protein produced in culture was fractionated by SDS-PAGE and immunodetected with a labeled antibody raised against the C-terminal portion of AAT, as shown in FIG. 5. Lane 4 is human AAT, and its migration position corresponds to about 52 kdal. In lane 3 is the plant-produced AAT, having an apparent molecular weight of about 49–50 kdal, indicating an extent of glycosylation of up to 60–80% of the glycosylation found in human AAT (non-glycosylated AAT has a molecular weight of 45 kdal).

Figure 7:
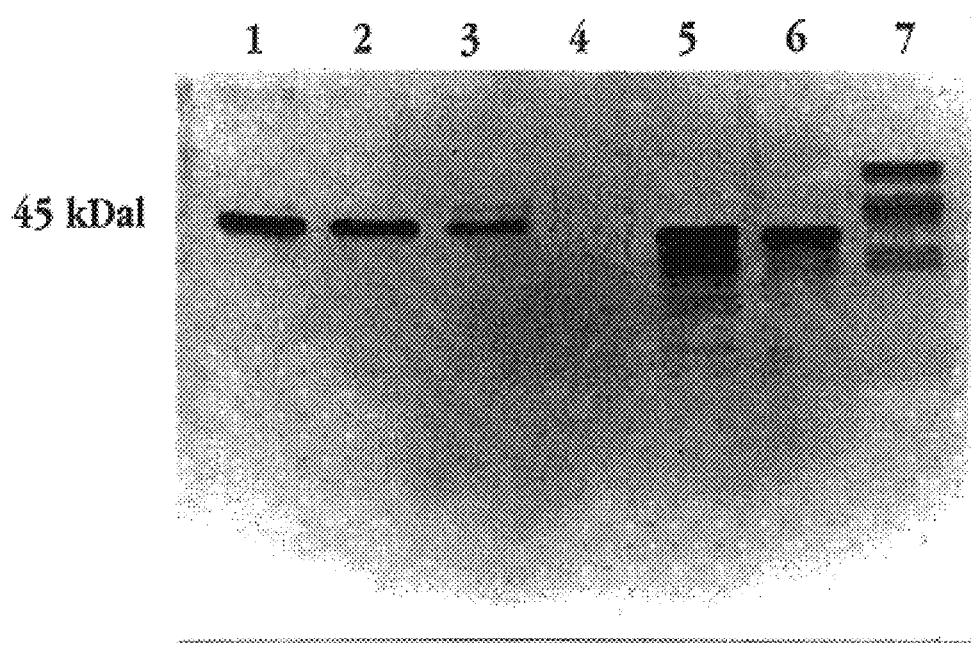
FIG. 7 shows Western blot analysis of AAT produced by transformed rice cell lines 18F, 11B, and 27F.

Similar results are shown in the Western blots in FIG. 7. Lanes 1–3 in this figure correspond to decreasing amount (15, 10, and 5 ng) of human AAT; lane 4, to 10 μl supernatant from a non-expressing plant cell line; lanes 5 and 6, to 10 μl supernatant from AAT-expressing plant cell lines 11B and 27F, respectively, and lane 7, to 10 μl supernatant from cell line 27F plus 250 ng trypsin. The upward mobilty shift in lane 7 is indicative of an association between trypsin and the plant-produced AAT.

Figures 6, 8:
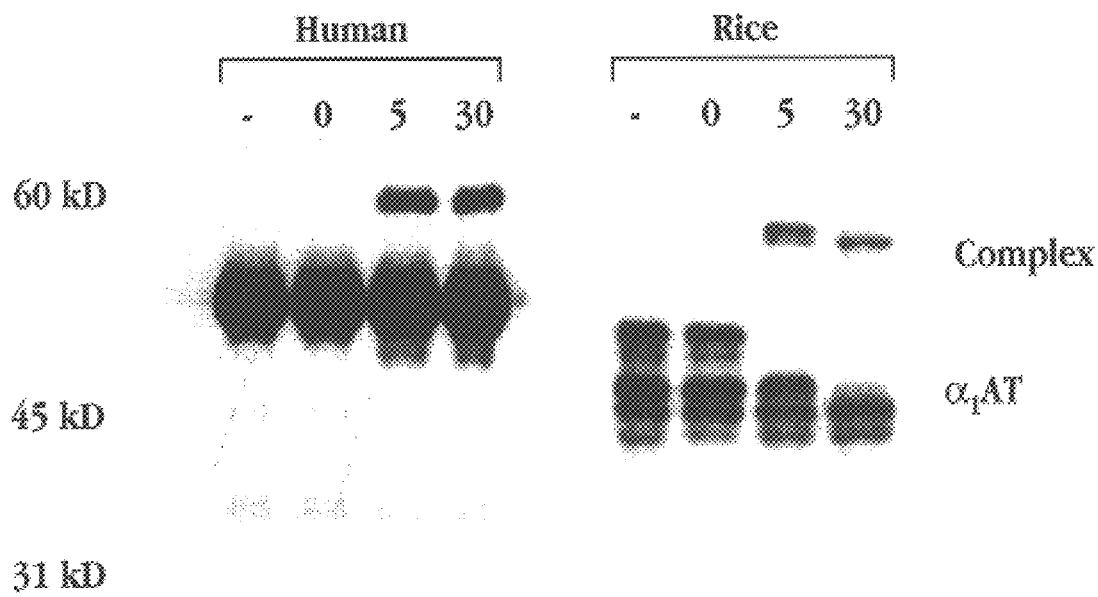
FIG. 6 shows the time course of elastase:AAT complex formation in human and rice-produced forms of AAT.
FIG. 8 shows an N-terminal sequence for mature $\alpha_1$-antitrypsin produced in accordance with the invention.

The ability of plant-produced AAT to bind to elastase is demonstrated in FIG. 6, which shows the shift in molecular weight over a 30 minute binding interval for the 52 kdal human AAT (lanes 1–4) and the 49–50 kdal plant-produced AAT.

To demonstrate that the mature protein is produced in secreted form, with the desired N-terminus, a chimeric gene constructed as above, and having the coding sequence for mature $\alpha_1$-antitrypsin was expressed and secreted in cell culture as described in Example 2. The isolated protein was then sequenced at its N-terminal region, yielding the N-terminal sequence shown in FIG. 8. This sequence, which is identified herein as SEQ ID NO:7, has the same N-terminal residue as native mature $\alpha_1$-antitrypsin.

IV. AAT Production in Germinating Seeds

In this embodiment, monocot cells transformed as above are used to regenerate plants, seeds from the plants are harvested and then germinated, and AAT is isolated from the germinated seeds.

Plant regeneration from cultured protoplasts or callus tissue is carried by standard methods, e.g., as described in Evans et al., *HANDBOOK OF PLANT CELL CULTURES*, Vol. 1: (MacMillan Publishing Co. New York, 1983); and Vasil I. R. (Ed.), *CELL CULTURE AND SOMATIC CELL GENETICS OF PLANTS*, Acad. Press, Orlando, Vol. I, 1984, and Vol. III, 1986, and as described in the above-cited PCT application.

A. Seed Germination Conditions

The transgenic seeds obtained from the regenerated plants are harvested, and prepared for germination by an initial steeping step, in which the seeds immersed in or sprayed with water to increase the moisture content of the seed to between 35–45%. This initiates germination. Steeping typically takes place in a steep tank which is typically fitted with a conical end to allow the seed to flow freely out. The addition of compressed air to oxygenate the steeping process is an option. The temperature is controlled at approximately 22° C. depending on the seed.

After steeping, the seeds are transferred to a germination compartment which contains air saturated with water and is under controlled temperature and air flows. The typical temperatures are between 12–25° C. and germination is permitted to continue for from 3 to 7 days.

Where the AAT coding gene is operably linked to a inducible promoter requiring a metabolite such as sugar or plant hormone, e.g., 2.5 to 100 μM gibberellic acid, this metabolite is added, removed or depleted from the steeping water medium and/or is added to the water saturated air used during germination. The seed absorbs the aqueous medium and begins to germinate expressing the heterologous protein. The medium may then be withdrawn and the malting begun, by maintaining the seeds in a moist temperature controlled aerated environment. In this way, the seeds may begin growth prior to expression, so that the expressed product is less likely to be partially degraded or denatured during the process.

More specifically, the temperature during the imbibition or steeping phase will be maintained in the range of about 15–25° C., while the temperature during the germination will usually be about 20° C. The time for the imbibition will usually be from about 2 to 4 days, while the germination time will usually be an additional 2 to 10 days, more usually 3 to 7 days. Usually, the time for the malting does not exceed about ten days. The period for the malting can be reduced by using plant hormones during the imbibition, particularly gibberellic acid.

To achieve maximum production of recombinant protein from malting, the malting procedure may be modified to accommodate de-hulled and de-embryonated seeds, as described in above-cited PCT application WO 95/14099. In the absence of sugars from the endosperm, there is expected to be a 5 to 10 fold increase in RAmy3D promoter activity and thus expression of AAT. Alternatively when embryoless-half seeds are incubated in 10 mM CaCl2 and 5 μM gibberellic acid, there is a 50 fold increase in RAmy1A promoter activity.

B. Isolation of AAT

After optimum germination and expression of the AAT gene have been achieved, the seeds are mashed (for example, by gentle grinding) to disrupt tissues and remove the hulls from the seeds. The seed mash is suspended in a protein extraction buffer. Such a buffer typically contains protease inhibitors, reducing agents and a buffering agent (such as, "TRIS" or sodium or potassium phosphate), and has a preferred pH of between 5–6.

The mash is agitated or stirred to ensure that all secreted protein is freed from tissues and cells. Large particulate matter, such as hull, plant tissues, and other debris are then removed by filtration or centrifugation. The supernatant is collected and chilled to reduce proteolysis of AAT.

The supernatant is subjected to various purification schemes used in the wet-milling industry (e.g., hydrocloning and ion exclusion chromatography) to remove un-wanted proteins and to concentrate AAT. Alternatively, ammonium sulfate precipitation can also be used to concentrate the AAT.

Affinity- and ion-exchange chromatography can be used to purify the AAT away from other proteins in the supernatant. The presence of AAT in the various chromatographic fractions can be detected using standard photometric assays.

In another embodiment, after the transgenic seeds are transported to a malting facility (malthouse) they are dehulled and de-embryonated (i.e., mechanical separation of the embryos and endosperm portions of the seed). The embryos and endosperms are separately soaked (steeped) in water for 48 hours. The seeds are treated as described above. The separated embryos are treated as follows. Expression of the RAmy3D promoters is induced in the absence of sugar and/or by the addition of chemicals, such as a plant hormone, e.g., absissic acid.

After optimum germination and expression of the AAT gene have been achieved, the embryo and endosperm portions are mixed and then mashed (i.e., gentle grinding) to disrupt seed tissues. The mash is then treated as above for purification of AAT.

V. Plant-Glycosylated AAT

In another aspect, the present invention relates to AAT having the sequence identified as SEQ ID NO:1, or a sequence homologous thereto, and the glycosylation pattern characteristic to monocot plant-cell synthesis, e.g., rice cell biosynthesis.

The following examples are provided by way of illustration only and not by way of limitation. Those of skill will readily recognize a variety of noncritical parameters which could be changed or modified to yield essentially similar results.

General Methods

Generally, the nomenclature and laboratory procedures with respect to standard recombinant DNA technology can be found in Sambrook, et al., *MOLECULAR CLONING: A LABORATORY MANUAL,* Cold Spring Harbor Laboratory, Cold Spring Harbor, N.Y. (1989) and in S. B. Gelvin and R. A. Schilperoot, *PLANT MOLECULAR BIOLOGY* (1988). Other general references are provided throughout this document. The procedures therein are known in the art and are provided for the convenience of the reader.

EXAMPLE 1

Construction of AAT-Expression Transformation Vectors Construction of p3D v1.0 Plasmid A. Hygromycin Resistance Gene Insertion The 3 kb BamHI fragment containing the 35S promoter-Hph-NOS was removed from the plasmid pMON410 (Monsanto, St. Louis, Mo.) and placed into an site-directed mutagenized BglII site in the pUC18 at 1463 to form the plasmid pUCH18+.

B. Terminator Insertion pOSg1ABK5 is a 5 kb BamHI-KpnI fragment from lambda clone λOSg1A (Huang, N., et al., (1990) Nuc. Acids Res. 18:7007) cloned into pBluescript KS- (Stratagene, San Diego, Calif.). Plasmid pOSg1ABK5 was digested with MspI and blunted with T4 DNA polymerase followed by SpeI digestion. The 350 bp terminator fragment was subcloned into pUC19 (New England BioLabs, Beverly, Mass.), which had been digested with BamHI, blunted with T4 DNA polymerase and digested with XbaI, to form pUC19/terminator.

C. RAmy3D Promoter Insertion

A 1.1 kb NheI-PstI fragment derived from p1AS1.5 (Huang, N. et al. *Plant Mol. Biol.* 23:737–747 (1993)), was cloned into the vector pGEM5zf- [multiple cloning site (MCS) (Promega, Madison, Wis.): ApaI, AatII, SphI, NcoI, SstII, EcoRV, SpeI, NotI, PstI, SalI, NdeI, SacI, MluI, NsiI] at the SpeI and PstI sites to form pGEM5zf-(3D/NheI-PstI). pGEM5zf-(3/NheI-PstI) was then digested with PstI and SacI, and two non-kinased 30mers having the complementary sequences 5' GCTTG ACCTG TAACT CGGGC CAGGC GAGCT 3' (SEQ ID NO:8) and 5' CGCCT AGCCC GAGTT ACAGG TCAAG CAGCT 3' (SEQ ID NO:9) were ligated in to form p3DProSig. The promoter fragment prepared by digesting p3DProSig with NcoI, blunting with T4 DNA polymerase, and digesting with SstI was subcloned into pUC19/terminator which had been digested with EcoRI, blunted with T4 DNA polymerase and digested with SstI, to form p3DProSigEND.

D. Multiple Cloning Site Insertion p3DProSigEND was digested with SstI and SmaI followed by the ligation of a new synthetic linker fragment constructed with the non-kinased complementary oligonucleotides 5' AGCTC CATGG CCGTG GCTCG AGTCT AGACG CGTCC CC 3' (SEQ ID NO:10) and 5' GGGGA CGCGT CTAGA CTCGA GCCAC GGCCA TGG 3' (SEQ ID NO:11) to form p3DProSigENDlink.

E. p3DProSigENDlink Flanking Site Modification p3DProSigENDlink was digested with SalI and blunted with T4 DNA polymerase followed by EcoRV digestion. The blunt fragment was then inserted into pBluescript KS+ (Stratagene) in the EcoRV site so that the HindIII site is proximal to the promoter and the EcoRI is proximal to the terminator sequence. The HindIII-EcoRI fragment was then moved into the polylinker of pUCH18+ to form the p3Dv1.0 expression vector.

F. RAmy1A Promoter Insertion

A 1.9 kb NheI-PstI fragment derived from subclone pOSG2CA2.3 from lambda clone λOSg2 (Huang et al., *Plant Mol. Biol.* 14:655–668 (1990)), was cloned into the vector pGEM5zf- at the SpeI and PstI sites to form pGEM5zf-(1A/NheI-PstI). pGEM5zf-(1A/NheI-PstI) was digested with PstI and SacI and two non-kinased 35mers and four kinased 32mers were ligated in, with the complementary sequences as follows: 5' GCATG CAGGT GCTGA ACACC ATGGT GAACA AACAC 3' (SEQ ID NO:12); 5' TTCTT GTCCC TTTCG GTCCT CATCG TCCTC CT 3' (SEQ ID NO:13); 5' TGGCC TCTCC TCCAA CTTGA CAGCC GGGAG CT 3' (SEQ ID NO:14); 5' TTCAC CATGG TGTTC AGCAC CTGCA TGCTG CA 3' (SEQ ID NO:15); 5' CGATG AGGAC CGAAA GGGAC AAGAA GTGTT TG 3' (SEQ ID NO:16); 5' CCCGG CTGTC AAGTT GGAGG AGAGG CCAAG GAGGA 3' (SEQ ID NO:17) to form p1AProSig. The HindIII-SacI 0.8 kb promoter fragment was subcloned from p1AProSig into the p3Dv1.0 vector digested with HindIII-SacI to yield the p1Av1.0 expression vector.

G. Construction of p3D-AAT Plasmid

Two PCR primers were used to amplify a fragment encoding AAT according to the sequence disclosed as Genbank Accession No. K01396: N-terminal primer 5' GAGGA TCCCC AGGGA GATGC TGCCC AGAA 3' (SEQ ID NO:18) and C-terminal primer 5' CGCGC TCGAG TTATT TTTGG GTGGG ATTCA CCAC 3' (SEQ ID NO:19). The N-terminal primer amplifies to a blunt site in frame with the end of the p3Dv1.0 signal peptide and the C-terminal primer contains a XhoI site for cloning the fragment into the vector as shown in FIG. 2A.

H. Construction of p3D-AAT Codon-Optimized Plasmid

The vector described above was modified as follows. The HindIII-EcoRI expression cassette fragment from p3Dv1.0 was moved into a NarI-lacking (Klenow filled) version of pUC19, creating p3Dv2.0. The HindIII-XbaI promoter fragment was cloned into pBluscript KS+ and a NotI site was introduced by means of a mutagenic oligonucleotide with the sequence 5' CCGTG TTCGA TAGTG AGCGG CCGCT AACCA CTACT GATC 3' (SEQ ID NO:20). This mutagenized fragment was then placed back into p3Dv2.0 resulting in p3Dv2.0 (NotI). A synthesized, codon-optimized RAmy3D signal peptide-mature AAT NotI/XhoI fragment (SEQ ID NO:6) was then cloned into the NotI/XhoI sites of p3Dv2.0 (NotI) forming p3D-AAT2.0. The NotI site was then used to insert the first exon (partial)-intron 1-second exon (partial) generated by PCR from pOSg1ABK5 with the NotI containing primers 5' GTTTC AGCTT ACACA GATGC GGCCG CCACC AGCAG CTTGT GT 3' (SEQ ID NO:21) and 5' CCTTT CAACA TGTTG TAGCG GCCGC CCTGC TGCTT CCACG 3' (SEQ ID NO:22) to create p3D-AAT2.1.1.

EXAMPLE 2

AAT Induction in Cell Culture

After selection of transgenic callus, callus cells were suspended in liquid culture containing AA2 media (Thompson, et al., Plant Science 47:123 (1986)), at 3% sucrose, pH 5.8. Thereafter, the cells were shifted to phosphate-buffered media (20 mM phosphate buffer, pH 6.8) using 10 mL multi-well tissue culture plates and shaken at 120 rpm in the dark for 48 hours. The supernatant was then removed and stored at −80° C. prior to western blot analysis.

Supernatants were concentrated using Centricon -10 filters (Amicon cat. #4207; Danvers, Mass.) and washed with induction media to remove substances interfering with electrophoretic migration. Samples were concentrated approximately 10 fold. Concentrated samples were treated with an effective concentration of 1 mM PMSF for 2–5 minutes to inactivate all serine protease activity. Band-shift assays to detect binding to elastase were carried out essentially as described in Owen, et al., J. Biol. Chem. 260:4384–4389 (1985)).

Treated samples were used for SDS-PAGE using the Laemmli system with 14% per-case NOvex gels and electroblotted using ½× towbin buffer in the Novex transblot unit. Blots were blocked in 5% non-fat dried milk, incubated overnight at 1:3000 dilution of the primary antibody (Dako rabbit polyclonal anti-antitrypsin, catalog No. A0012). After three washes in PBS (pH 7) the blots were incubated with 1:3000 dilution of the goat anti-rabbit antibody (BioRad 170–6518; Richmond, Calif.) for one hour. The blots were then rinsed three times in TBS (pH 9.5) and developed in 40 mM NBT and 40 mM BCIP until the standards showed up clearly. Blots were then rinsed thoroughly in deionized water and air dried.

Although the invention has been described with reference to particular embodiments, it will be appreciated that a variety of changes and modifications can be made without departing from the invention.

It is claimed:

1. A method for producing a stable, glycosylated $\alpha_1$-antitrypsin (AAT) comprising the steps of:
   (a) obtaining rice or barley cells transformed with a chimeric gene having (i) an inducible transcriptional regulatory region, (ii) a first DNA sequence encoding AAT, and (iii) a second DNA sequence encoding a signal polypeptide, where said second DNA sequence is operably linked to said transcriptional regulatory region and said first DNA sequence, and where said signal polypeptide is in translation-frame with said AAT and is effective to facilitate secretion of expressed AAT from the transformed cells,
   (b) cultivating the transformed cells under conditions effective to induce the promoter, thereby to promote expression of AAT and secretion of the protein from the transformed cells; and
   (c) isolating AAT produced by the cells.

2. The method of claim 1, where said first DNA sequence has the sequence identified by SEQ ID NO:3.

3. The method of claim 1, wherein the transformed cells are callus cells, said promoter is upregulated by sugar-depletion in cell culture, and said cultivating includes culturing the cells in a cell culture medium depleted in sugar.

4. the method of claim 3, wherein the promoter is a rice $\alpha$-amylase RAmy3D or RAmy3E promoter.

5. The method of claim 1, wherein the transformed cells are aleurone cells of mature seeds, said promoter is upregulated during seed germination, and said cultivating includes germinating said seeds, either in embryonated or de-embryonated form.

6. The method of claim 5, wherein the promoter is a rice $\alpha$-amylase RAmy1A promoter.

7. The method of claim 1, wherein the signal polypeptide has the sequence identified by SEQ ID NO:4.

8. The method of claim 1, wherein the signal polypeptide has the sequence identified by SEQ ID NO:5.

9. A DNA coding sequence for expression of $\alpha_1$ antitrypsin (AAT) in rice or barley plants, comprising the sequence identified by SEQ ID NO:3.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 394 amino acids
        (B) TYPE: amino acid
        (D) TOPOLOGY: linear (ii) MOLECULE TYPE: protein (vii) IMMEDIATE SOURCE:
        (B) CLONE: mature AAT amino acid sequence (xi) SEQUENCE DESCRIPTION: SEQ ID NO:1:

Glu Asp Pro Gln Gly Asp Ala Ala Gln Lys Thr Asp Thr Ser His His

```
              1               5              10              15
        Asp Gln Asp His Pro Thr Phe Asn Lys Ile Thr Pro Asn Leu Ala Glu
                         20                  25                  30

Phe Ala Phe Ser Leu Tyr Arg Gln Leu Ala His Gln Ser Asn Ser Thr
                     35                  40                  45

Asn Ile Phe Phe Ser Pro Val Ser Ile Ala Thr Ala Phe Ala Met Leu
                     50                  55                  60

Ser Leu Gly Thr Lys Ala Asp Thr His Asp Glu Ile Leu Glu Gly Leu
         65                  70                  75                  80

Asn Phe Asn Leu Thr Glu Ile Pro Glu Ala Gln Ile His Glu Gly Phe
                         85                  90                  95

Gln Glu Leu Leu Arg Thr Leu Asn Gln Pro Asp Ser Gln Leu Gln Leu
                     100                 105                 110

Thr Thr Gly Asn Gly Leu Phe Leu Ser Glu Gly Leu Lys Leu Val Asp
                     115                 120                 125

Lys Phe Leu Glu Asp Val Lys Lys Leu Tyr His Ser Glu Ala Phe Thr
         130                 135                 140

Val Asn Phe Gly Asp Thr Glu Glu Ala Lys Lys Gln Ile Asn Asp Tyr
         145                 150                 155                 160

Val Glu Lys Gly Thr Gln Gly Lys Ile Val Asp Leu Val Lys Glu Leu
                     165                 170                 175

Asp Arg Asp Thr Val Phe Ala Leu Val Asn Tyr Ile Phe Phe Lys Gly
                     180                 185                 190

Lys Trp Glu Arg Pro Phe Glu Val Lys Asp Thr Glu Glu Glu Asp Phe
                     195                 200                 205

His Val Asp Gln Val Thr Thr Val Lys Val Pro Met Met Lys Arg Leu
         210                 215                 220

Gly Met Phe Asn Ile Gln His Cys Lys Lys Leu Ser Ser Trp Val Leu
         225                 230                 235                 240

Leu Met Lys Tyr Leu Gly Asn Ala Thr Ala Ile Phe Phe Leu Pro Asp
                     245                 250                 255

Glu Gly Lys Leu Gln His Leu Glu Asn Glu Leu Thr His Asp Ile Ile
                     260                 265                 270

Thr Lys Phe Leu Glu Asn Glu Asp Arg Arg Ser Ala Ser Leu His Leu
                     275                 280                 285

Pro Lys Leu Ser Ile Thr Gly Thr Tyr Asp Leu Lys Ser Val Leu Gly
         290                 295                 300

Gln Leu Gly Ile Thr Lys Val Phe Ser Asn Gly Ala Asp Leu Ser Gly
         305                 310                 315                 320

Val Thr Glu Glu Ala Pro Leu Lys Leu Ser Lys Ala Val His Lys Ala
                     325                 330                 335

Val Leu Thr Ile Asp Glu Lys Gly Thr Glu Ala Ala Gly Ala Met Phe
                     340                 345                 350

Leu Glu Ala Ile Pro Met Ser Ile Pro Pro Glu Val Lys Phe Asn Lys
                     355                 360                 365

Pro Phe Val Phe Leu Met Ile Glu Gln Asn Thr Lys Ser Pro Leu Phe
         370                 375                 380

Met Gly Lys Val Val Asn Pro Thr Gln Lys
         385                 390
```

(2) INFORMATION FOR SEQ ID NO:2:

(i) SEQUENCE CHARACTERISTICS:
        (A) LENGTH: 1185 base pairs (B) TYPE: nucleic acid
            (C) STRANDEDNESS: single
            (D) TOPOLOGY: linear (vii) IMMEDIATE SOURCE:
            (B) CLONE: native AAT coding sequence (xi) SEQUENCE DESCRIPTION: SEQ ID NO:2:

```
GAGGATCCCC AGGGAGATGC TGCCCAGAAG ACAGATACAT CCCACCATGA TCAGGATCAC      60

CCAACCTTCA ACAAGATCAC CCCCAACCTG GCTGAGTTCG CCTTCAGCCT ATACCGCCAG     120

CTGGCACACC AGTCCAACAG CACCAATATC TTCTTCTCCC CAGTGAGCAT CGCTACAGCC     180

TTTGCAATGC TCTCCCTGGG GACCAAGGCT GACACTCACG ATGAAATCCT GGAGGGCCTG     240

AATTTCAACC TCACGGAGAT TCCGGAGGCT CAGATCCATG AAGGCTTCCA GGAACTCCTC     300

CGTACCCTCA ACCAGCCAGA CAGCCAGCTC CAGCTGACCA CCGGCAATGG CCTGTTCCTC     360

AGCGAGGGCC TGAAGCTAGT GGATAAGTTT TTGGAGGATG TTAAAAAGTT GTACCACTCA     420

GAAGCCTTCA CTGTCAACTT CGGGGACACC GAAGAGGCCA AGAAACAGAT CAACGATTAC     480

GTGGAGAAGG GTACTCAAGG GAAAATTGTG GATTTGGTCA AGGAGCTTGA CAGAGACACA     540

GTTTTTGCTC TGGTGAATTA CATCTTCTTT AAAGGCAAAT GGGAGAGACC CTTTGAAGTC     600

AAGGACACCG AGGAAGAGGA CTTCCACGTG GACCAGGTGA CCACCGTGAA GGTGCCTATG     660

ATGAAGCGTT TAGGCATGTT TAACATCCAG CACTGTAAGA AGCTGTCCAG CTGGGTGCTG     720

CTGATGAAAT ACCTGGGCAA TGCCACCGCC ATCTTCTTCC TGCCTGATGA GGGGAAACTA     780

CAGCACCTGG AAAATGAACT CACCCACGAT ATCATCACCA AGTTCCTGGA AAATGAAGAC     840

AGAAGGTCTG CCAGCTTACA TTTACCCAAA CTGTCCATTA CTGGAACCTA TGATCTGAAG     900

AGCGTCCTGG GTCAACTGGG CATCACTAAG GTCTTCAGCA ATGGGGCTGA CCTCTCCGGG     960

GTCACAGAGG AGGCACCCCT GAAGCTCTCC AAGGCCGTGC ATAAGGCTGT GCTGACCATC    1020

GACGAGAAAG GGACTGAAGC TGCTGGGGCC ATGTTTTTAG AGGCCATACC CATGTCTATC    1080

CCCCCCGAGG TCAAGTTCAA CAAACCCTTT GTCTTCTTAA TGATTGAACA AAATACCAAG    1140

TCTCCCCTCT TCATGGGAAA AGTGGTGAAT CCCACCCAAA AATAA                    1185
```

(2) INFORMATION FOR SEQ ID NO:3:

(i) SEQUENCE CHARACTERISTICS:
            (A) LENGTH: 1185 base pairs
            (B) TYPE: nucleic acid
            (C) STRANDEDNESS: single
            (D) TOPOLOGY: linear (vii) IMMEDIATE SOURCE:
            (B) CLONE: codon-optimized AAT coding sequence (xi) SEQUENCE DESCRIPTION: SEQ ID NO:3:

```
GAGGACCCGC AGGGCGACGC CGCCCAGAAG ACCGACACCA GCCACCACGA CCAGGACCAC      60

CCGACGTTCA ACAAGATCAC CCCGAATTTG GCCGAATTCG CCTTCAGCCT GTACCGCCAG     120

CTCGCGCACC AGTCCAACTC CACCAACATC TTCTTCAGCC CGGTGAGCAT CGCCACCGCC     180

TTCGCCATGC TGTCCCTGGG TACCAAGGCG GACACCCACG ACGAGATCCT CGAAGGGCTG     240

AACTTCAACC TGACGGAGAT CCCGGAGGCG CAGATCCACG AGGGCTTCCA GGAGCTGCTC     300

AGGACGCTCA ACCAGCCGGA CTCCCAGCTC CAGCTCACCA CCGGCAACGG GCTCTTCCTG     360

TCCGAGGGCC TCAAGCTCGT CGATAAGTTC CTGGAGGACG TGAAGAAGCT CTACCACTCC     420

GAGGCGTTCA CCGTCAACTT CGGGGACACC GAGGAGGCCA AGAAGCAGAT CAACGACTAC     480
```

```
GTCGAGAAGG GGACCCAGGG CAAGATCGTG GACCTGGTCA AGGAATTGGA CAGGGACACC     540

GTCTTCGCGC TCGTCAACTA CATCTTCTTC AAGGGCAAGT GGGAGCGCCC GTTCGAGGTG     600

AAGGACACCG AGGAGGAGGA CTTCCACGTC GACCAGGTCA CCACCGTCAA GGTCCCGATG     660

ATGAAGAGGC TCGGCATGTT CAACATCCAG CACTGCAAGA AGCTCTCCAG CTGGGTGCTC     720

CTCATGAAGT ACCTGGGGAA CGCCACCGCC ATCTTCTTCC TGCCGGACGA GGGCAAGCTC     780

CAGCACCTGG AGAACGAGCT GACGCACGAC ATCATCACGA AGTTCCTGGA GAACGAGGAC     840

AGGCGCTCCG CTAGCCTCCA CCTCCCGAAG CTGAGCATCA CCGGCACGTA CGACCTGAAG     900

AGCGTGCTGG GCCAGCTGGG CATCACGAAG GTCTTCAGCA ACGGCGCGGA CCTCTCCGGC     960

GTGACGGAGG AGGCCCCCCT GAAGCTCTCC AAGGCCGTGC ACAAGGCGGT GCTCACGATC    1020

GACGAGAAGG GGACGGAAGC TGCCGGGGCC ATGTTCCTGG AGGCCATCCC CATGTCCATC    1080

CCGCCCGAGG TCAAGTTCAA CAAGCCCTTC GTCTTCCTGA TGATCGAGCA GAACACGAAG    1140

AGCCCCCTCT TCATGGGGAA GGTCGTCAAC CCCACGCAGA AGTGA                    1185
```

(2) INFORMATION FOR SEQ ID NO:4:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (vii) IMMEDIATE SOURCE:
        (B) CLONE: RAmy3D signal peptide (xi) SEQUENCE DESCRIPTION: SEQ ID NO:4:

```
Met Lys Asn Thr Ser Ser Leu Cys Leu Leu Leu Val Val Leu Cys
 1               5                  10                  15

Ser Leu Thr Cys Asn Ser Gly Gln Ala
            20                  25
```

(2) INFORMATION FOR SEQ ID NO:5:

(i) SEQUENCE CHARACTERISTICS:
        (A) LENGTH: 25 amino acids
        (B) TYPE: amino acid
        (D) TOPOLOGY: linear (ii) MOLECULE TYPE: protein (vii) IMMEDIATE SOURCE:
        (B) CLONE: RAmy1A signal peptide (xi) SEQUENCE DESCRIPTION: SEQ ID NO:5:

```
Met Val Asn Lys His Phe Leu Ser Leu Ser Val Leu Ile Val Leu Leu
 1               5                  10                  15

Gly Leu Ser Ser Asn Leu Thr Ala Gly
            20                  25
```

(2) INFORMATION FOR SEQ ID NO:6:

(i) SEQUENCE CHARACTERISTICS:
        (A) LENGTH: 1308 base pairs
        (B) TYPE: nucleic acid
        (C) STRANDEDNESS: single
        (D) TOPOLOGY: linear (vii) IMMEDIATE SOURCE:
        (B) CLONE: codon-optimized NotI/XhoI fragment encoding RAmy3D
            signal peptide-AAT fusion protein (xi) SEQUENCE DESCRIPTION: SEQ ID NO:6:

GCGGCCGCTC ACTATCGAAC ACGGTTTCAG CTTACACAGA TATGAAGAAC ACCTCCTCCC    60

TCTGCCTCCT GCTGCTCGTG GTCCTCTGCT CCCTGACCTG CAACAGCGGC CAGGCGGAGG   120

ACCCGCAGGG CGACGCCGCC CAGAAGACCG ACACCAGCCA CCACGACCAG GACCACCCGA   180

CGTTCAACAA GATCACCCCG AATTTGGCCG AATTCGCCTT CAGCCTGTAC CGCCAGCTCG   240

CGCACCAGTC CAACTCCACC AACATCTTCT TCAGCCCGGT GAGCATCGCC ACCGCCTTCG   300

CCATGCTGTC CCTGGGTACC AAGGCGGACA CCCACGACGA GATCCTCGAA GGGCTGAACT   360

TCAACCTGAC GGAGATCCCG GAGGCGCAGA TCCACGAGGG CTTCCAGGAG CTGCTCAGGA   420

CGCTCAACCA GCCGGACTCC CAGCTCCAGC TCACCACCGG CAACGGGCTC TTCCTGTCCG   480

AGGGCCTCAA GCTCGTCGAT AAGTTCCTGG AGGACGTGAA GAAGCTCTAC CACTCCGAGG   540

CGTTCACCGT CAACTTCGGG GACACCGAGG AGGCCAAGAA GCAGATCAAC GACTACGTCG   600

AGAAGGGGAC CCAGGGCAAG ATCGTGGACC TGGTCAAGGA ATTGGACAGG GACACCGTCT   660

TCGCGCTCGT CAACTACATC TTCTTCAAGG GCAAGTGGGA GCGCCCGTTC GAGGTGAAGG   720

ACACCGAGGA GGAGGACTTC CACGTCGACC AGGTCACCAC CGTCAAGGTC CCGATGATGA   780

AGAGGCTCGG CATGTTCAAC ATCCAGCACT GCAAGAAGCT CTCCAGCTGG GTGCTCCTCA   840

TGAAGTACCT GGGGAACGCC ACCGCCATCT TCTTCCTGCC GGACGAGGGC AAGCTCCAGC   900

ACCTGGAGAA CGAGCTGACG CACGACATCA TCACGAAGTT CCTGGAGAAC GAGGACAGGC   960

GCTCCGCTAG CCTCCACCTC CCGAAGCTGA GCATCACCGG CACGTACGAC CTGAAGAGCG  1020

TGCTGGGCCA GCTGGGCATC ACGAAGGTCT TCAGCAACGG CGCGGACCTC TCCGGCGTGA  1080

CGGAGGAGGC CCCCCTGAAG CTCTCCAAGG CCGTGCACAA GGCGGTGCTC ACGATCGACG  1140

AGAAGGGGAC GGAAGCTGCC GGGGCCATGT TCCTGGAGGC CATCCCCATG TCCATCCCGC  1200

CCGAGGTCAA GTTCAACAAG CCCTTCGTCT TCCTGATGAT CGAGCAGAAC ACGAAGAGCC  1260

CCCTCTTCAT GGGGAAGGTC GTCAACCCCA CGCAGAAGTG AGCTCGAG              1308

(2) INFORMATION FOR SEQ ID NO:7:

(i) SEQUENCE CHARACTERISTICS:
         (A) LENGTH: 13 amino acids
         (B) TYPE: amino acid
         (D) TOPOLOGY: linear (ii) MOLECULE TYPE: peptide (vii) IMMEDIATE SOURCE:
         (B) CLONE: N-terminal sequence of plant-produced mature AAT (xi) SEQUENCE DESCRIPTION: SEQ ID NO:7:

Glu Asp Pro Gln Gly Asp Ala Ala Gln Lys Thr Asp Thr
  1               5                  10

(2) INFORMATION FOR SEQ ID NO:8:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (xi) SEQUENCE DESCRIPTION: SEQ ID NO:8:

GCTTGACCTG TAACTCGGGC CAGGCGAGCT                                     30

(2) INFORMATION FOR SEQ ID NO:9:

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

CGCCTAGCCC GAGTTACAGG TCAAGCAGCT                                           30

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:10:

AGCTCCATGG CCGTGGCTCG AGTCTAGACG CGTCCCC                                   37

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:11:

GGGGACGCGT CTAGACTCGA GCCACGGCCA TGG                                       33

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:12:

GCATGCAGGT GCTGAACACC ATGGTGAACA AACAC                                     35

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:13:

TTCTTGTCCC TTTCGGTCCT CATCGTCCTC CT                                        32

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:14:

TGGCCTCTCC TCCAACTTGA CAGCCGGGAG CT                                        32

(2) INFORMATION FOR SEQ ID NO:15:
```

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:15:

TTCACCATGG TGTTCAGCAC CTGCATGCTG CA                                32

(2) INFORMATION FOR SEQ ID NO:16:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:16:

CGATGAGGAC CGAAAGGGAC AAGAAGTGTT TG                                32

(2) INFORMATION FOR SEQ ID NO:17:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:17:

CCCGGCTGTC AAGTTGGAGG AGAGGCCAAG GAGGA                             35

(2) INFORMATION FOR SEQ ID NO:18:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:18:

GAGGATCCCC AGGGAGATGC TGCCCAGAA                                    29

(2) INFORMATION FOR SEQ ID NO:19:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:19:

CGCGCTCGAG TTATTTTTGG GTGGGATTCA CCAC                              34

(2) INFORMATION FOR SEQ ID NO:20:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:20:

CCGTGTTCGA TAGTGAGCGG CCGCTAACCA CTACTGATC                         39

(2) INFORMATION FOR SEQ ID NO:21:

(i) SEQUENCE CHARACTERISTICS:

```
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:21:

GTTTCAGCTT ACACAGATGC GGCCGCCACC AGCAGCTTGT GT                42

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:22:

CCTTTCAACA TGTTGTAGCG GCCGCCCTGC TGCTTCCACG                   40
```